United States Patent
Cushing et al.

(10) Patent No.: US 12,370,073 B2
(45) Date of Patent: Jul. 29, 2025

(54) DEVICE FOR IMMOBILIZING A SHOULDER

(71) Applicant: Gen3 Medical, LLC, Fayetteville, GA (US)

(72) Inventors: Michael Cushing, Fayetteville, GA (US); Nikolaj Kloch, Mount Pleasant, SC (US); Russell Foley, Newnan, GA (US)

(73) Assignee: Gen3 Medical, LLC, Fayetteville, GA (US)

( * ) Notice: Subject to any disclaimer, the term of this patent is extended or adjusted under 35 U.S.C. 154(b) by 286 days.

(21) Appl. No.: 18/139,197

(22) Filed: Apr. 25, 2023

(65) Prior Publication Data

US 2023/0338183 A1    Oct. 26, 2023

Related U.S. Application Data

(60) Provisional application No. 63/334,778, filed on Apr. 26, 2022.

(51) Int. Cl.
*A61F 5/37* (2006.01)
(52) U.S. Cl.
CPC .................................. *A61F 5/3753* (2013.01)
(58) Field of Classification Search
CPC ........ A61F 5/3753; A61F 5/373; A61F 5/013; A61F 5/3738; A61F 5/01; A61F 5/02;
(Continued)

(56) References Cited

U.S. PATENT DOCUMENTS 5,569,172 A    10/1996  Padden et al.
5,665,058 A *   9/1997  Young .................... A61F 5/3753
                                                     602/20

(Continued)

FOREIGN PATENT DOCUMENTS

EP    0192181    5/1991
EP    3954343    2/2022
(Continued)

OTHER PUBLICATIONS

Cushing, Michael, et al.; International Preliminary Report on Patentability for Application No. PCT/US2023/019828 filed Apr. 25, 2023, mailed Nov. 7, 2024, 8 pages.
(Continued)

*Primary Examiner* — Alireza Nia
*Assistant Examiner* — Daniel A Miller
(74) *Attorney, Agent, or Firm* — Taylor Duma LLP

(57) ABSTRACT

A device immobilizes a shoulder joint and associated upper arm and forearm of a human patient in a selected relative position. The device comprises a platform including a planar base portion and a pair of opposed parallel side walls extending upwardly from the longitudinal edges of the base portion. The platform supportively receives and at least partially encloses the forearm of the patient. A mount defining a terminal slot is integral with at least one side wall. A belt is provided for securing around the waist of the patient. A belt clip attaches between the belt at a side of the body corresponding to the shoulder to be supported and the platform. The belt clip includes a lug projecting outwardly from the clip and corresponding in size and shape to the terminal slot for insertion into the slot, wherein the platform is suspended from the belt.

15 Claims, 20 Drawing Sheets

(58) Field of Classification Search
CPC .. A61F 5/05858; A61F 5/0118; A61F 5/3723; A61F 5/37; A61F 5/3746; A61F 200/0167; A61F 200/0179; A61F 200/0151; A61F 200/0158; A61F 200/0153; A61F 200/0172
USPC ......................................................... 128/878
See application file for complete search history.

(56) References Cited

U.S. PATENT DOCUMENTS

| | | | |
|---|---|---|---|
| 6,659,971 | B2 | 12/2003 | Gaylord |
| 6,932,781 | B2 | 8/2005 | Itoi |
| 7,563,236 | B2 | 7/2009 | Kazmierczak et al. |
| 8,454,544 | B2 | 6/2013 | Barnes et al. |
| 9,204,989 | B2 | 12/2015 | Begon et al. |
| 9,492,303 | B2 | 11/2016 | Golden et al. |
| 10,610,400 | B1 | 4/2020 | Krenzel |
| 10,736,767 | B2 | 8/2020 | Boileau et al. |
| 10,912,667 | B1 | 2/2021 | Sickles et al. |
| 11,234,851 | B2 | 2/2022 | Kaminsky et al. |
| 2007/0191746 | A1 | 8/2007 | Barnes et al. |
| 2010/0152635 | A1 | 6/2010 | Borden |
| 2014/0305442 | A1 | 10/2014 | Bergenudd et al. |
| 2014/0371644 | A1 | 12/2014 | Erbe et al. |
| 2015/0080776 | A1 | 3/2015 | Davis |
| 2015/0173936 | A1 | 6/2015 | Lowden |
| 2016/0022468 | A1 | 1/2016 | Lo |

FOREIGN PATENT DOCUMENTS

| | | |
|---|---|---|
| GB | 2292889 | 6/1998 |
| JP | 4098646 | 6/2008 |
| WO | 2023211953 | 11/2023 |

OTHER PUBLICATIONS

Cushing, Michael, et al.; International Search Report and Written Opinion for Application No. PCT/US2023/019828 filed Apr. 25, 2023, mailed Jun. 22, 2023, 10 pages.

\* cited by examiner

DEVICE FOR IMMOBILIZING A SHOULDER

CROSS-REFERENCE TO RELATED APPLICATIONS

This application claims the benefit of U.S. Provisional Application No. 63/334,778, filed Apr. 26, 2022, the teaching of which is incorporated herein in its entirety by reference.

BACKGROUND

An orthopedic device is described and, more particularly, a device for immobilizing a shoulder in a fixed position for use following surgery, or when suffering from an injury, for supporting the shoulder and arm with a belt around the waist.

Following shoulder surgery or a shoulder injury, the affected arm may be placed in a sling so that the shoulder remains motionless while it heals. A typical sling has a pouch that is supported by a strap around the wearer's neck. The wearer's forearm rests within the pouch such that the elbow is at a 90° angle and the forearm extends across the abdomen. The shoulder strap is connected to the pouch adjacent the elbow, extends across the back passing over the wearer's uninjured shoulder adjacent the neck, and connects to the other end of the pouch adjacent the hand. In some cases, an elevation support is provided, such as a foam cushion, which supports the arm and maintains the shoulder at certain angles of abduction, extension and rotation. A plurality of straps suspends the elevation support from the neck or shoulders.

Conventional shoulder slings can be very irritating and sometimes painful to a user thus decreasing compliance between the patient and intended usage. The strap exerts a potentially painful lateral force against the neck when the conventional sling is worn, which can irritate the neck, the back, and aggravate pre-existing neck problems.

For the foregoing reasons, there is a need for a device for immobilizing a shoulder that will allow a user to comfortably support the injured shoulder or arm.

SUMMARY

A device is provided for immobilizing a shoulder joint and associated upper arm and forearm of a human patient in a selected relative position. The device comprises a platform including a planar base portion and a pair of opposed parallel side walls extending upwardly from the longitudinal edges of the base portion. The platform supportively receives and at least partially encloses the forearm of the patient. A mount defining a terminal slot is integral with at least one side wall. A belt is provided for securing around the waist of the patient. A belt clip attaches between the belt at a side of the body corresponding to the shoulder to be supported and the platform. The belt clip includes a lug projecting outwardly from the clip and corresponding in size and shape to the terminal slot for insertion into the slot, wherein the platform is suspended from the belt.

In one aspect, the platform has opposed posterior slots in the side walls for slidably passing a strap through the slots and over the forearm for holding the forearm in the selected relative position.

In another aspect, the device may further comprise an opposed second mount integral with the opposite side wall, the second mount defining a terminal slot. Alternatively, a second mount is integral with the side wall and anteriorly spaced from the first mount, the second mount defining a terminal slot. With this feature, the device may further comprise an opposed pair of mounts integral with the opposite side wall, each of the second pair of mounts defining a terminal slot.

In another embodiment, a resilient wedge is provided for disposing between the platform and the torso of the patient, the wedge having a medial surface for abutting the torso of the patient and a lateral surface for operatively contacting the platform. In one aspect, a distance between anterior edges of the medial and lateral surfaces of the wedge is substantially greater than a distance between posterior edges of the medial and lateral surfaces of the wedge. With this feature, the platform has an anterior slot, and the device further comprises a strap for passing through the slot and around the belt for securing the wedge and the platform to the wearer. The platform may have an opposed anterior slot for use on the opposite side of the body.

Generally speaking, the platform is held in a generally horizontal position. In this aspect, the platform and the wedge retain the wearer's arm in a position of up to about 30° of abduction and up to about 30° of external rotation.

In another aspect, the shoulder immobilization device further comprises a second belt clip for attaching between the belt at a side of the body corresponding to the shoulder to be supported and the second mount on the platform. The second belt clip includes a lug projecting outwardly from the clip and corresponding in size and shape to the terminal slot in the second mount.

In yet another aspect, the first and second mounts are non-orthogonal with the base portion of the platform such that the anterior of the platform is higher than the posterior when suspended from the belt.

In another embodiment, a hand grip is provided adjacent an anterior end of the platform. The hand grip is selected from a ball, a gel pad, a post and combinations thereof. The anterior surface of the platform may define an opening for receiving at least a portion of the ball.

DESCRIPTION

Figure 1:
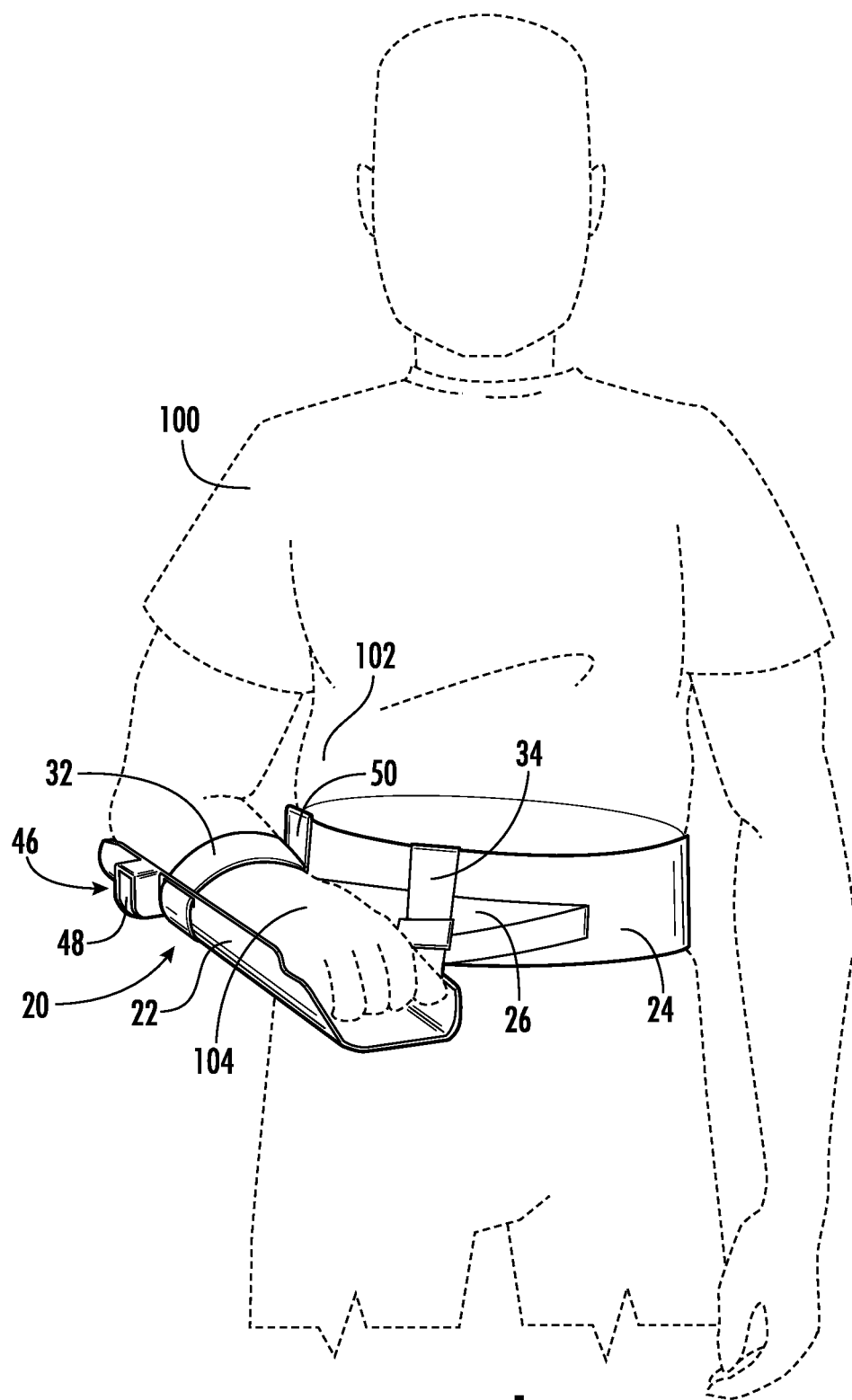
FIG. 1 is a front perspective view of a user shown in phantom wearing a first embodiment of a device for immobilizing a shoulder.
Figure 2:
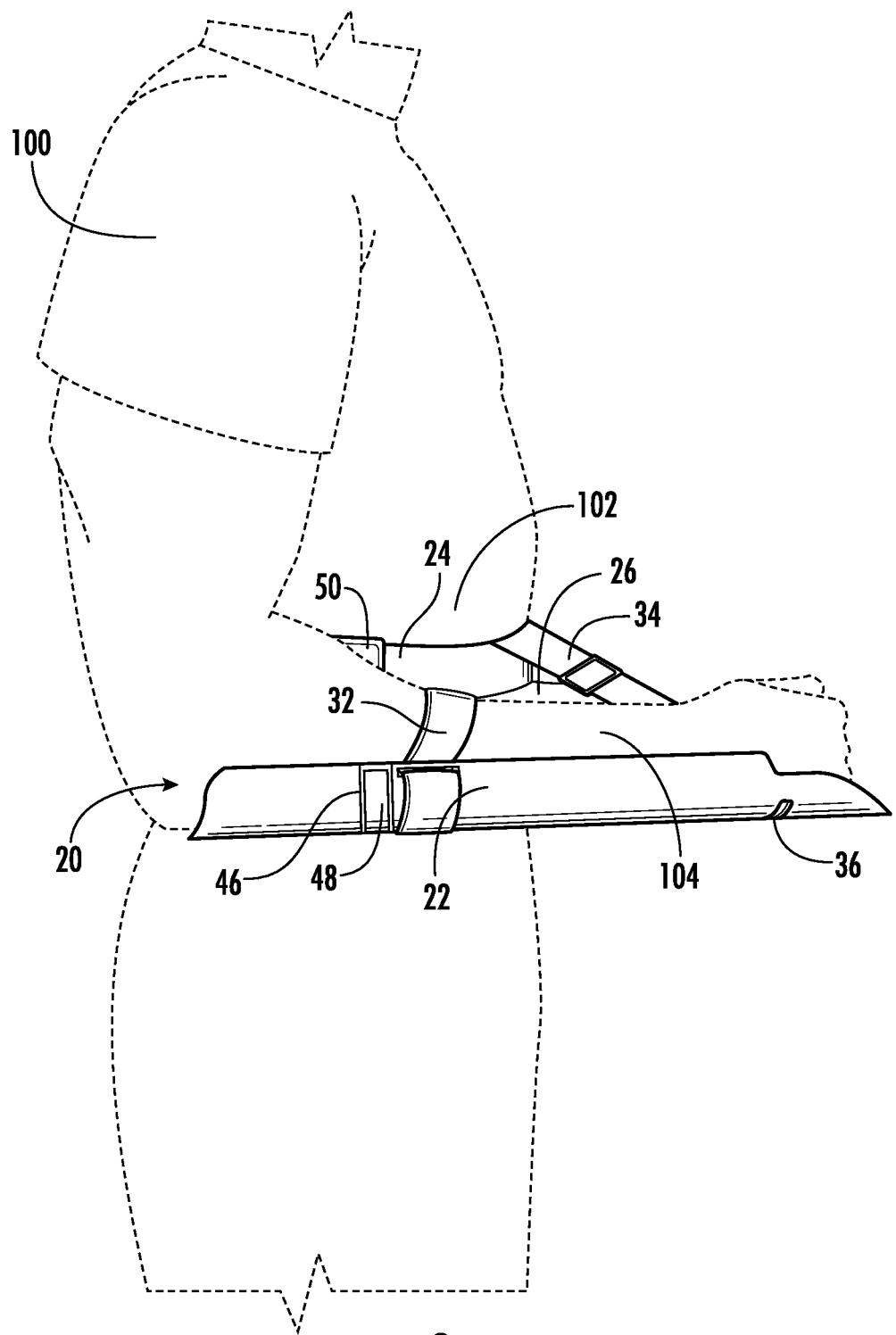
FIG. 2 is a side elevation view of the user wearing the shoulder immobilizer as shown in FIG. 1.
Figure 3:
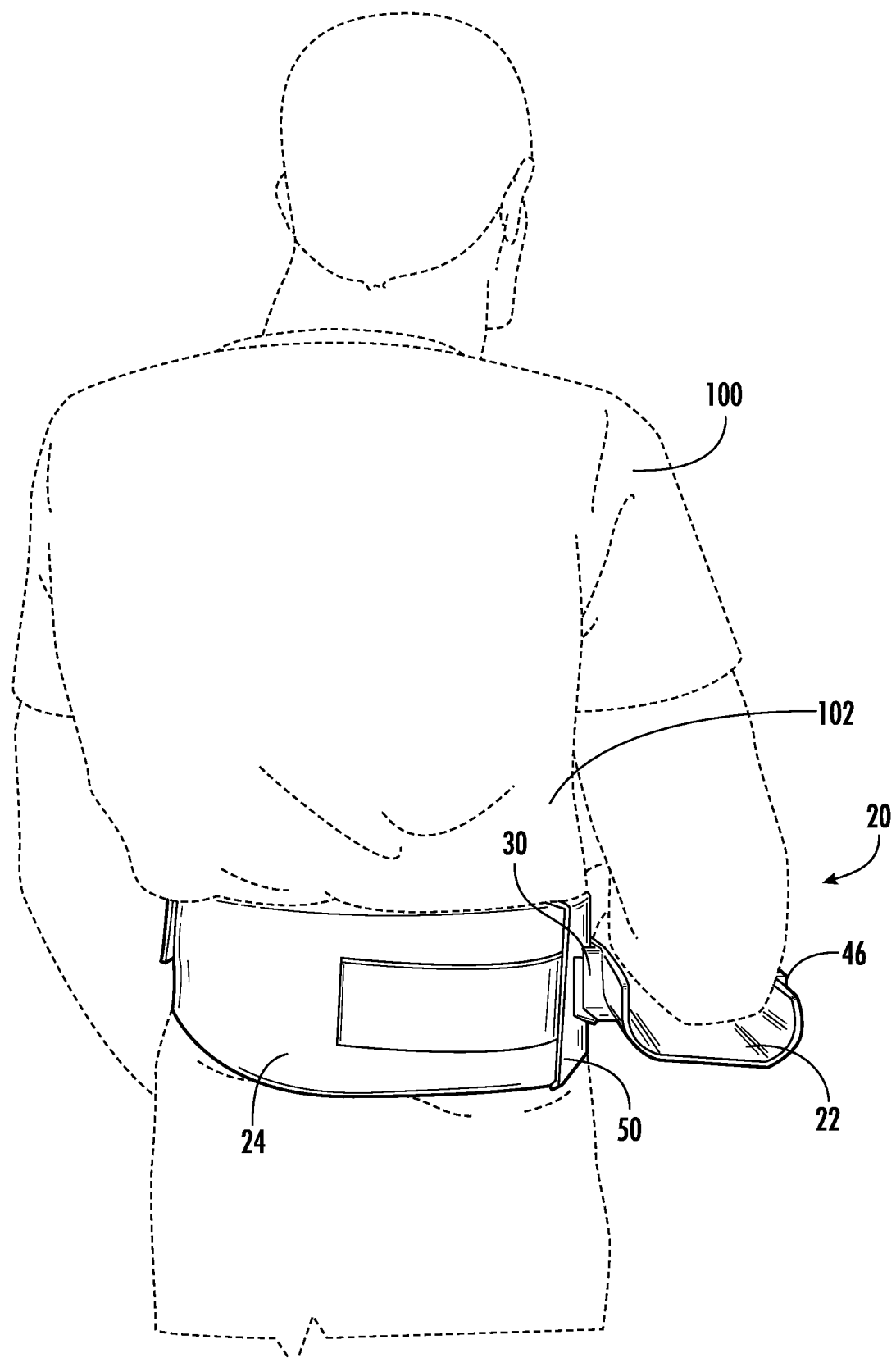
FIG. 3 is a rear elevation view of the user wearing the shoulder immobilizer as shown in FIG. 1.
Figure 4:
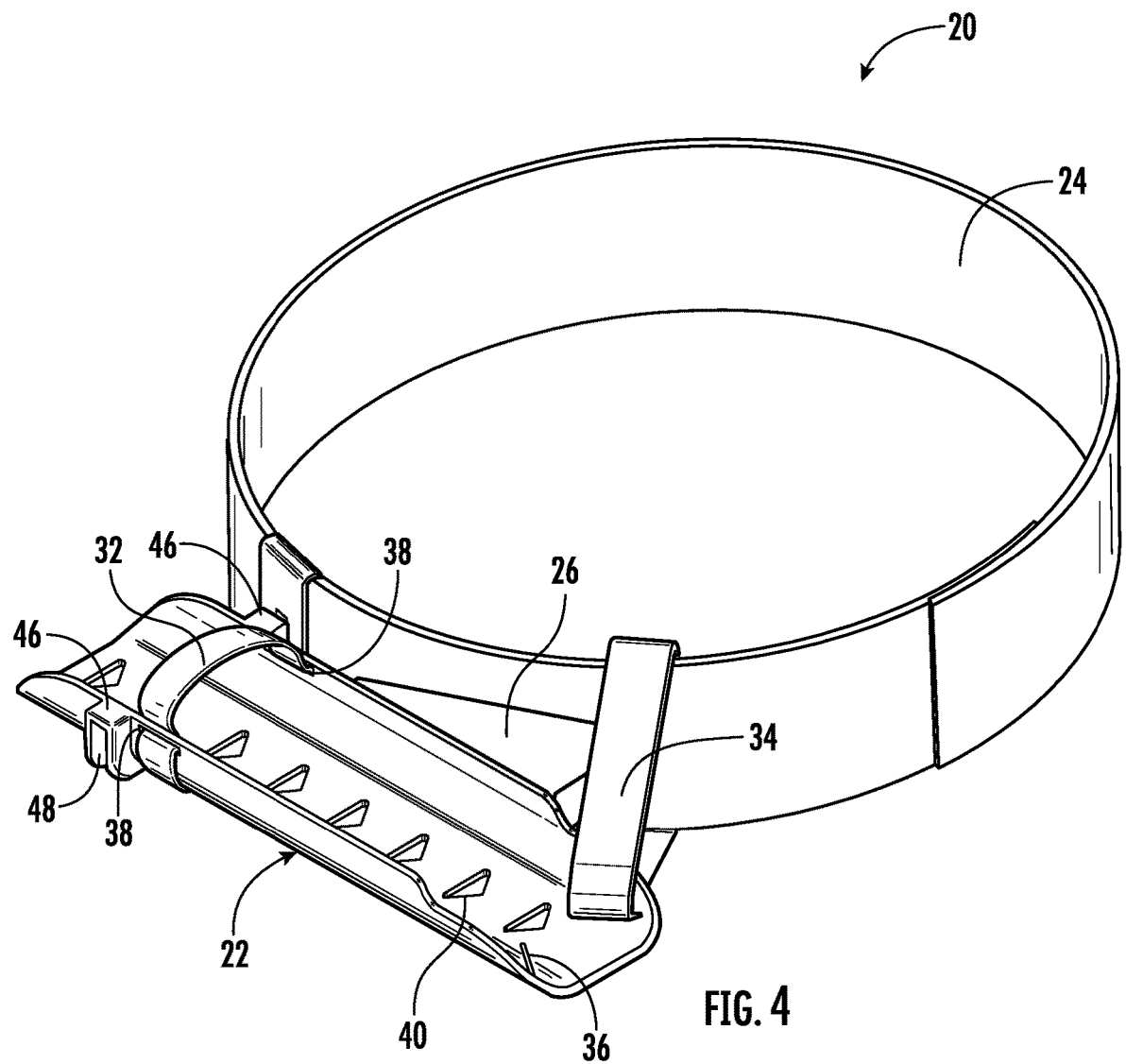
FIG. 4 is a front perspective view of the wearing the shoulder immobilizer as shown in FIG. 1 without the user.
Figure 5:
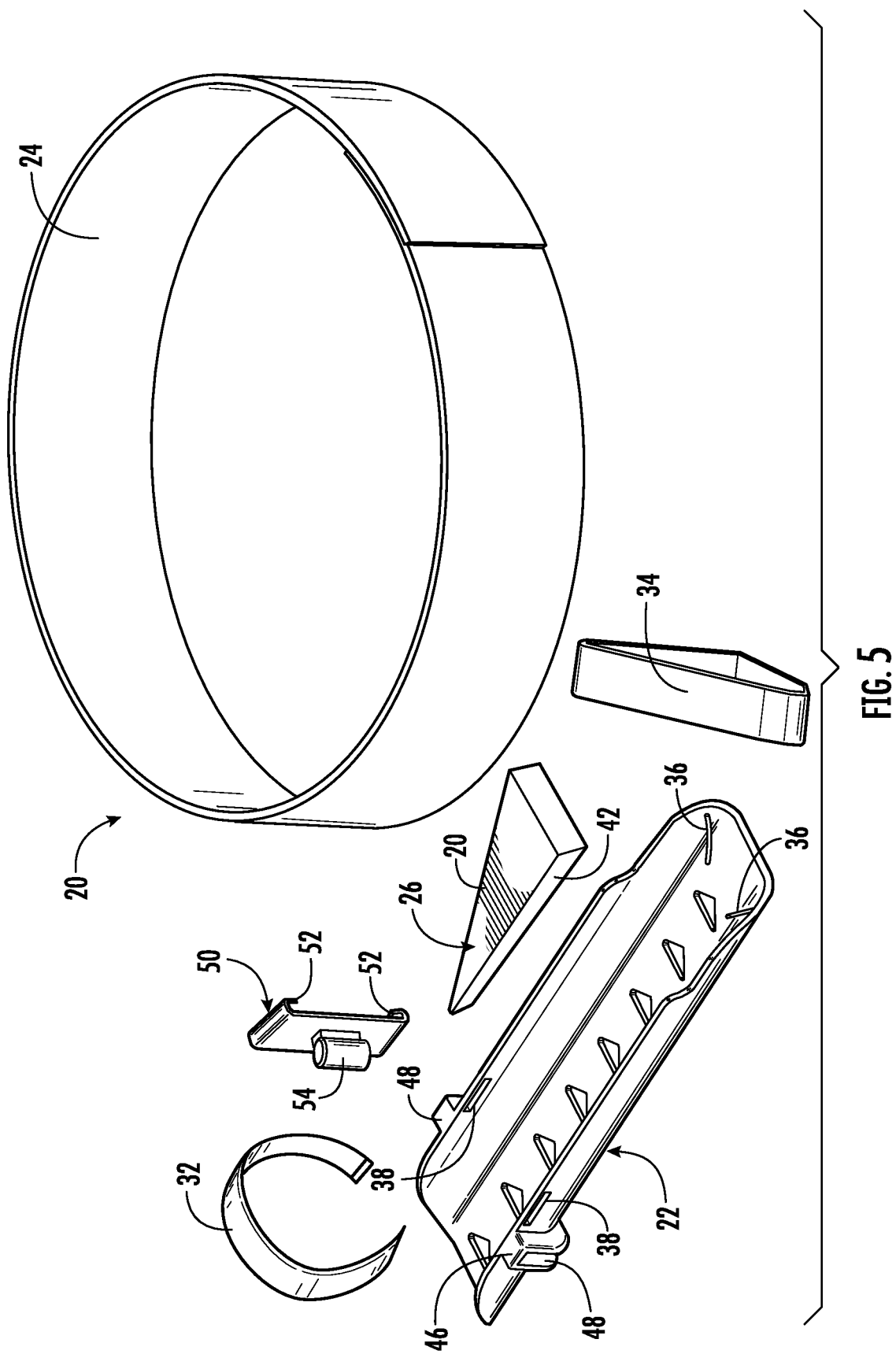
FIG. 5 is an exploded front perspective view of the shoulder immobilizer as shown in FIG. 4.
Figure 6A:
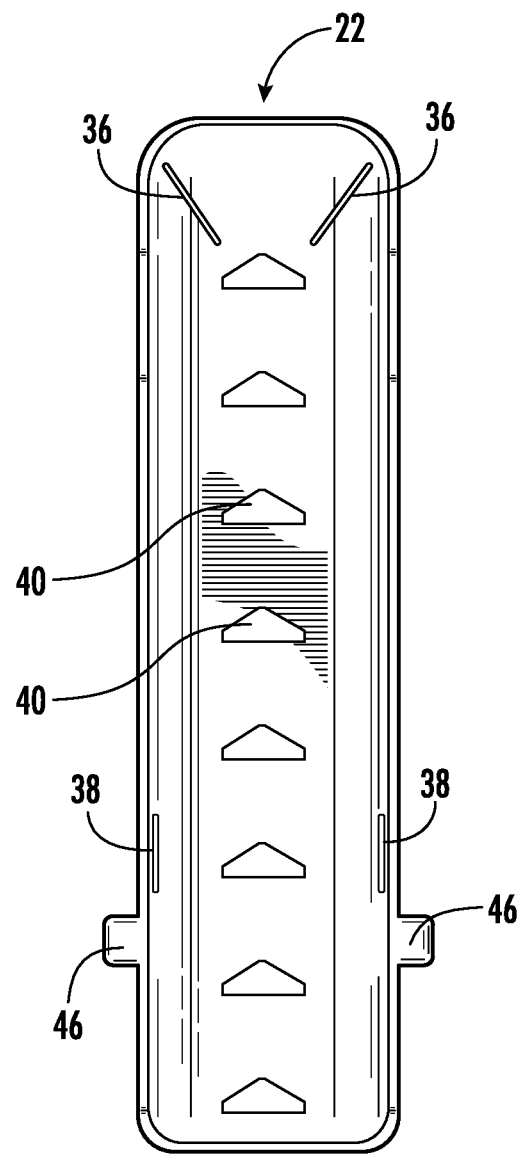
FIGS. 6A-6F are a top plan, bottom plan, right side elevation (the left side elevation being a mirror image thereof), front end elevation, rear end elevation and a longitudinal cross-section view, respectively, of a platform for use with the shoulder immobilizer as shown in FIG. 1.
Figure 6B:
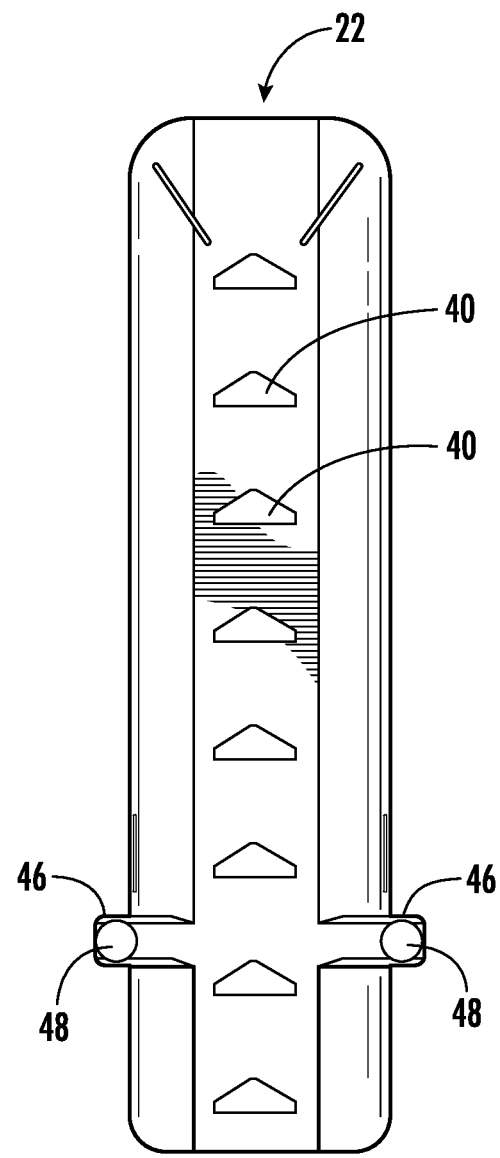
Figure 6C:
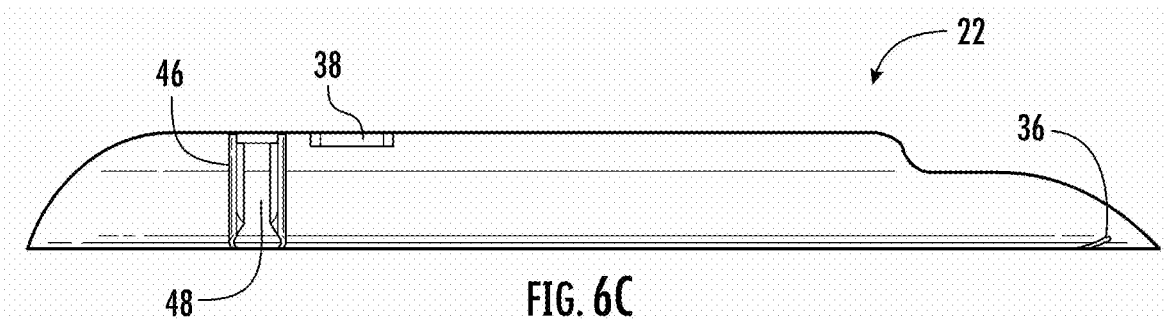
Figure 6D:
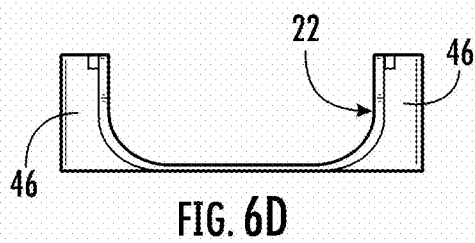
Figure 6E:
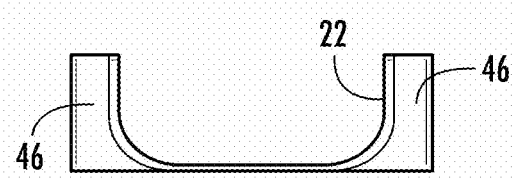
Figure 6F:
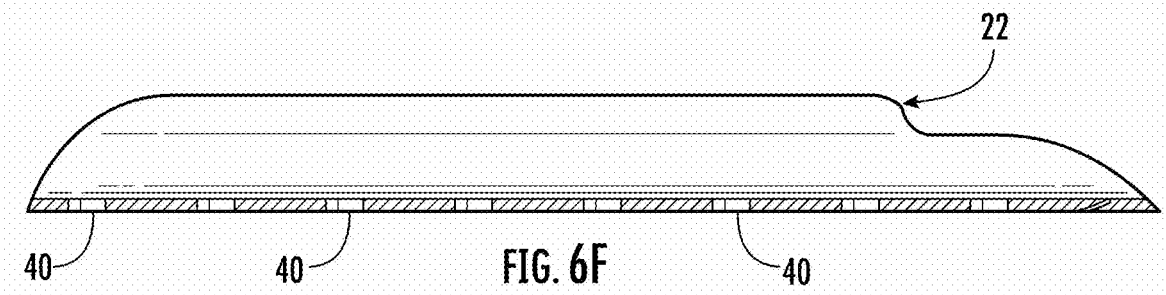
Figure 7A:
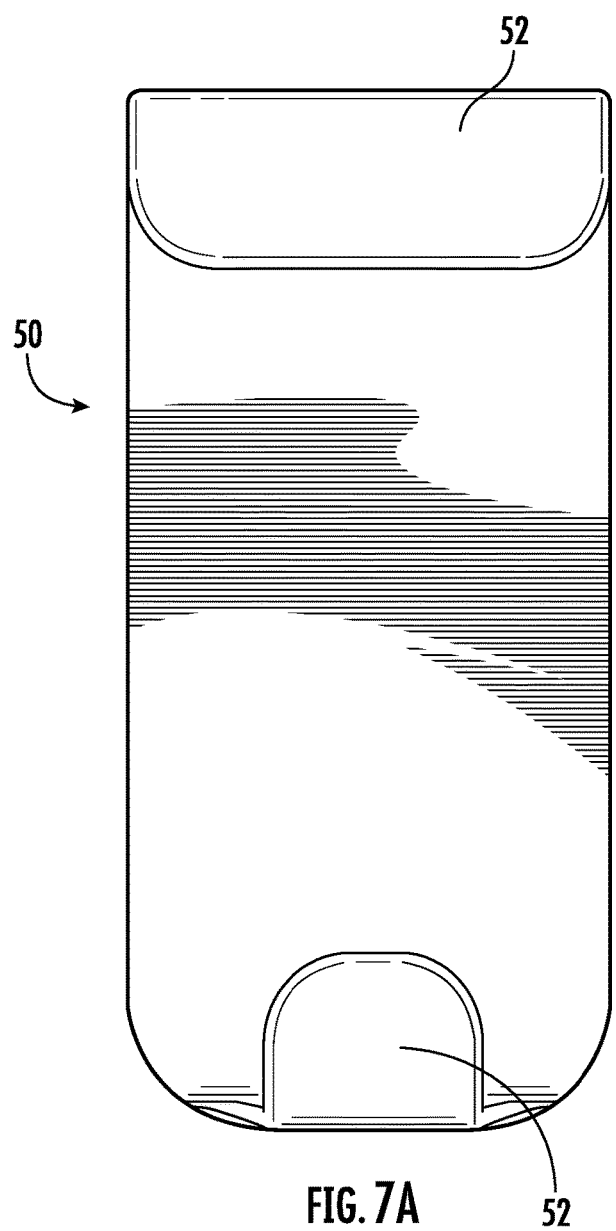
FIGS. 7A-7E are a front elevation, side elevation, rear elevation, top plan and bottom plan view, respectively, of a belt clip for use with the shoulder immobilizer as shown in FIG. 1.
Figure 7B:
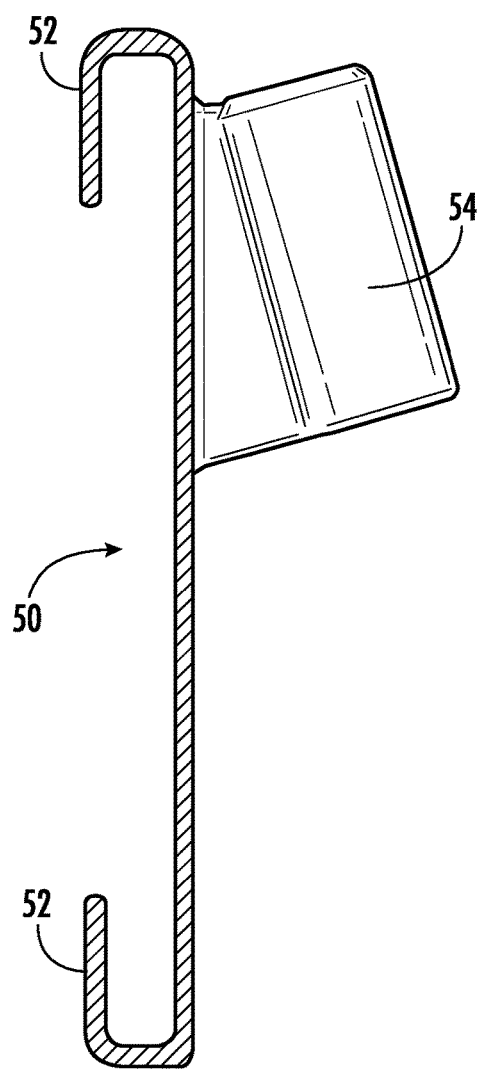
Figure 7C:
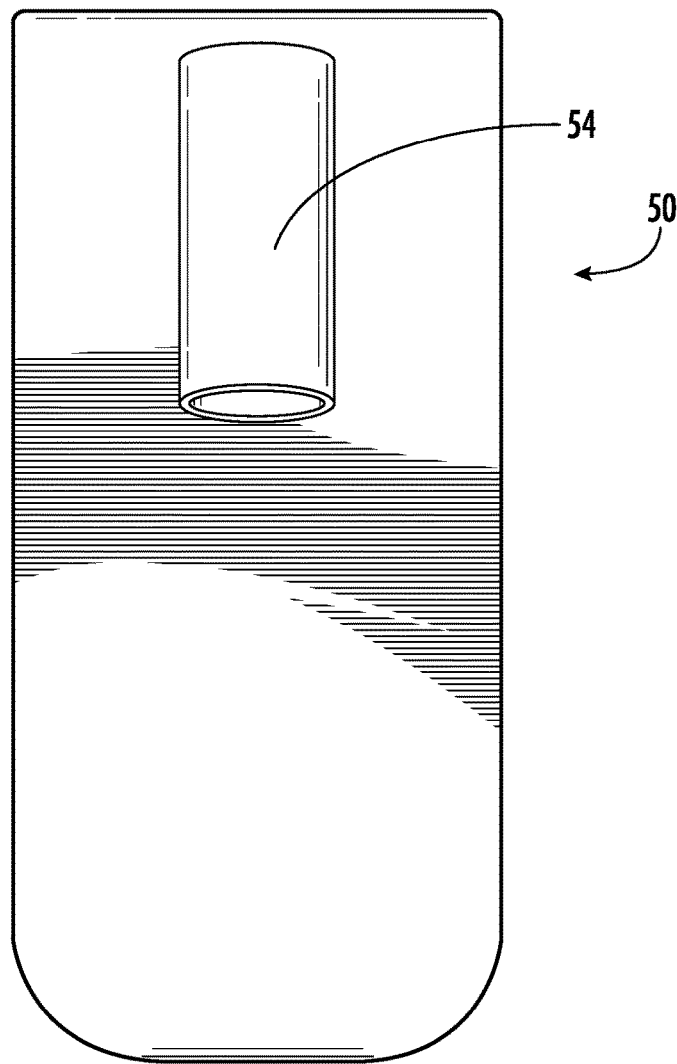
Figure 7D:
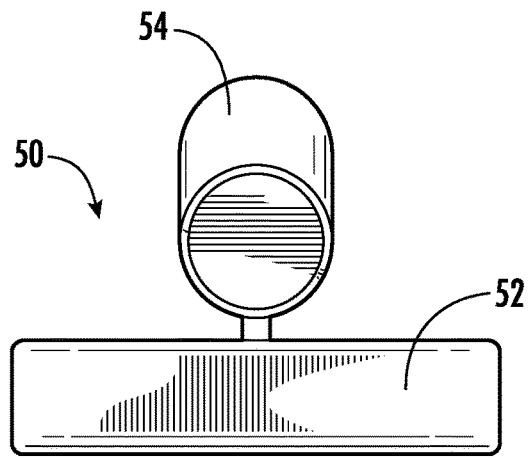
Figure 7E:
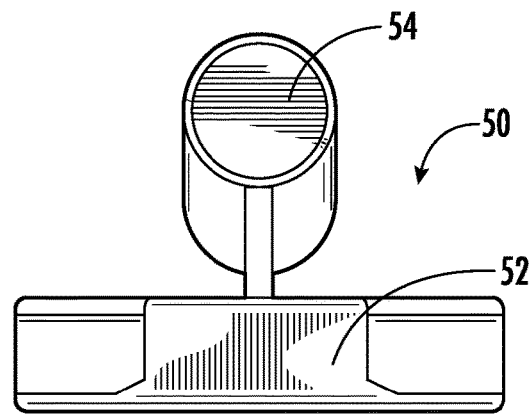
Figure 8:
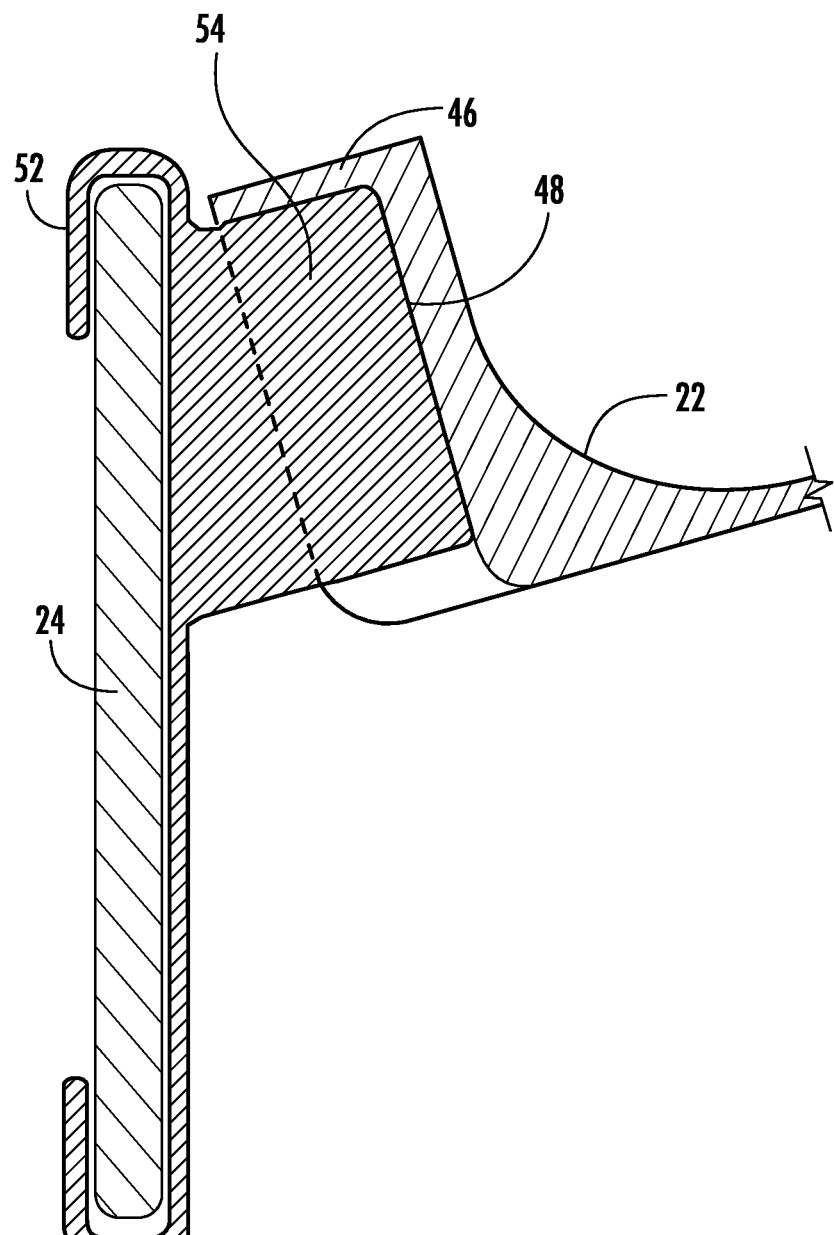
FIG. 8 is a vertical cross-section view of a connection assembly for use with the shoulder immobilizer as shown in FIG. 1.
Figure 9:
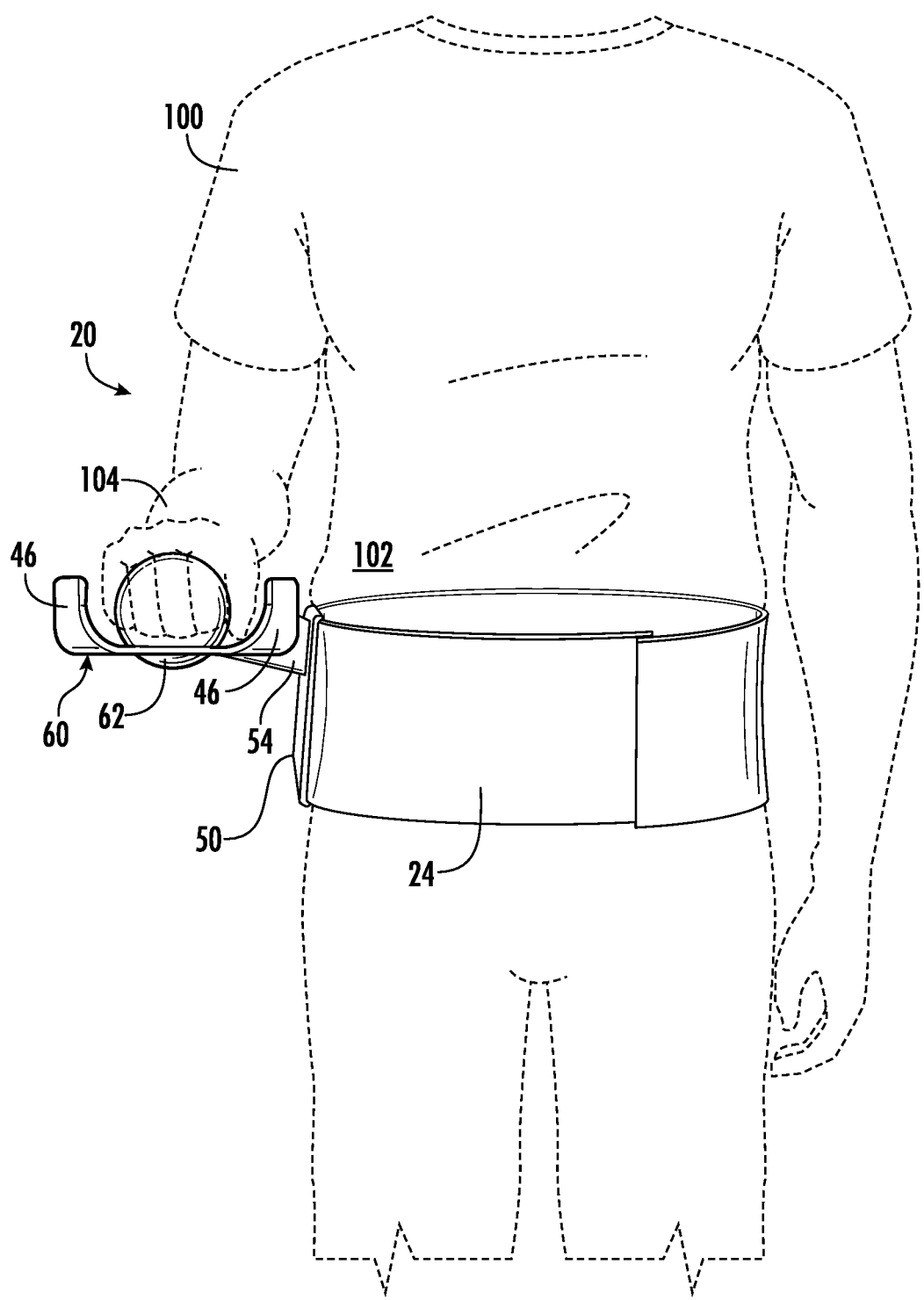
FIG. 9 is a front perspective view of a user shown in phantom wearing a second embodiment of a device for immobilizing a shoulder.
Figure 10:
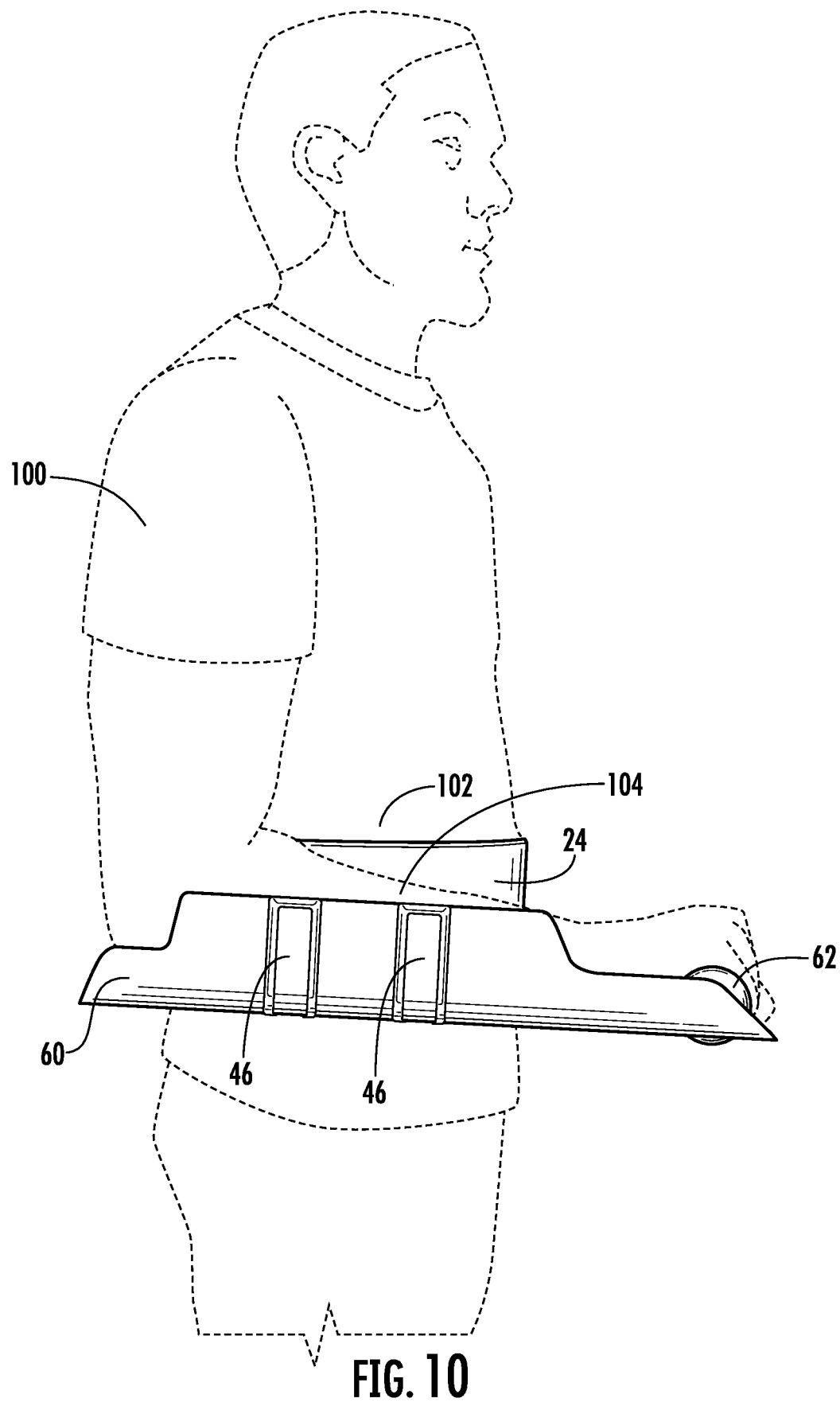
FIG. 10 is a side elevation view of the user wearing the shoulder immobilizer as shown in FIG. 9.
Figure 11:
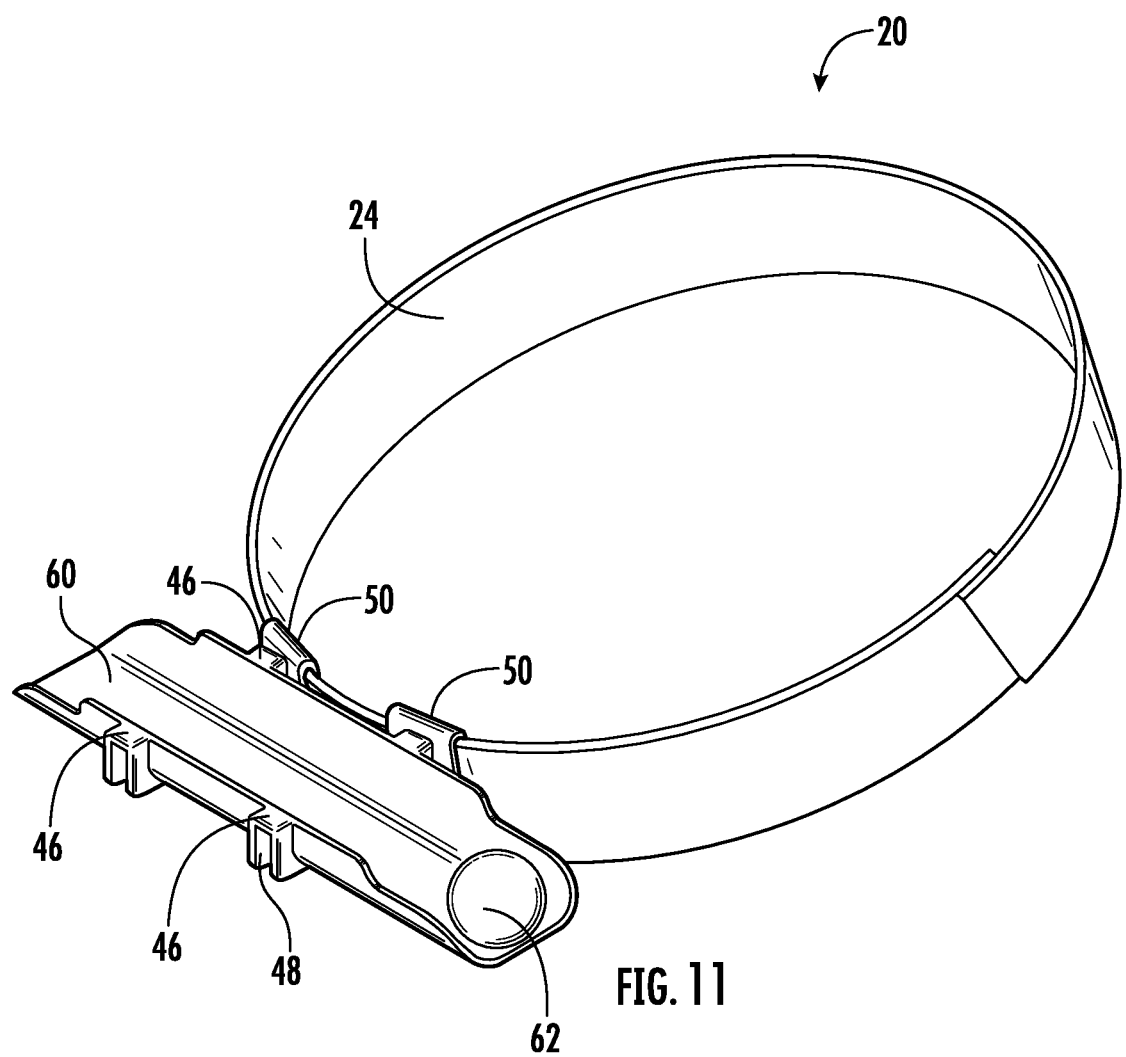
FIG. 11 is a front perspective view of the shoulder immobilizer as shown in FIG. 9 without the user.
Figure 12:
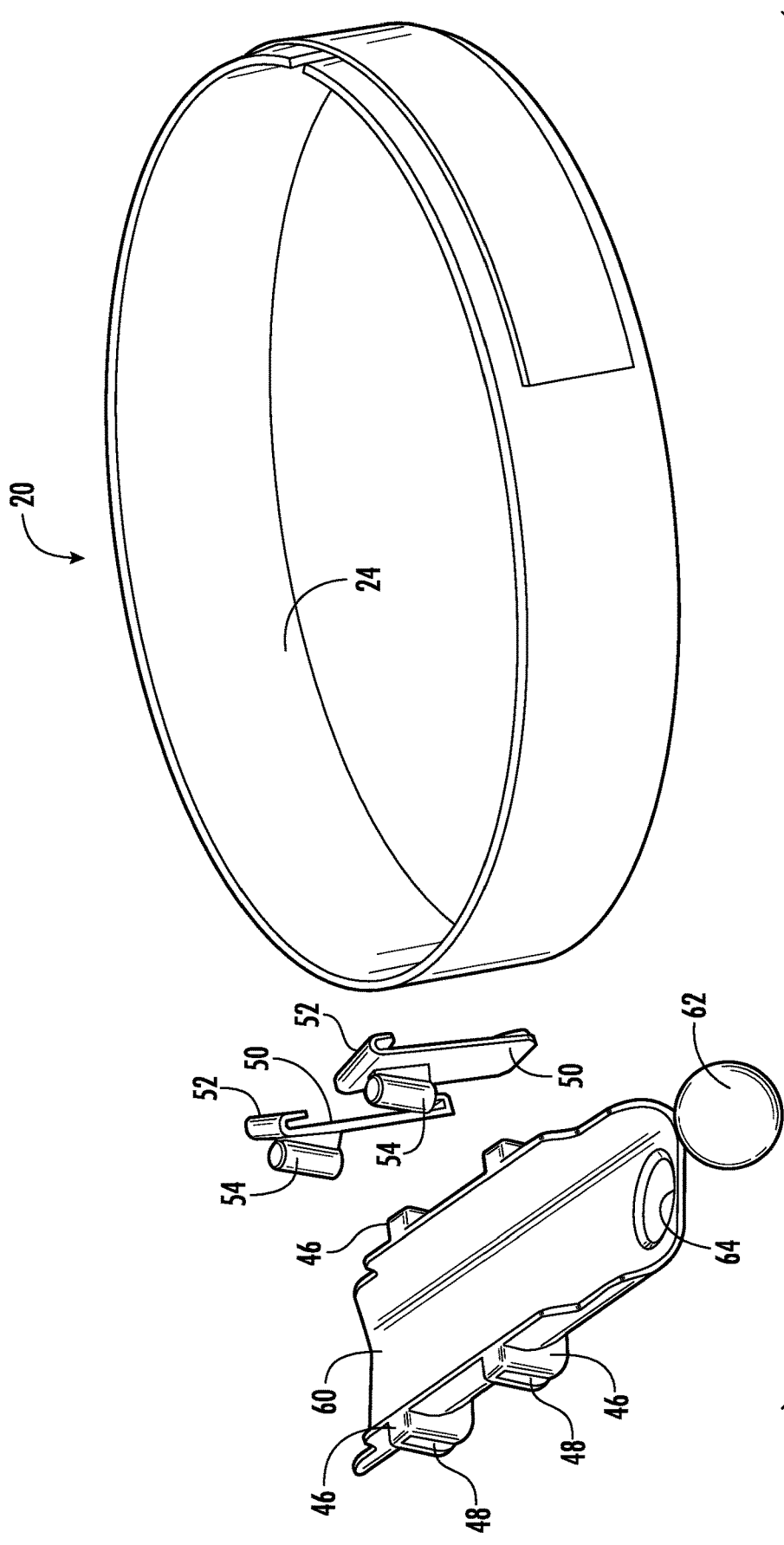
FIG. 12 is an exploded front perspective view of the shoulder immobilizer as shown in FIG. 9.
Figure 13A:
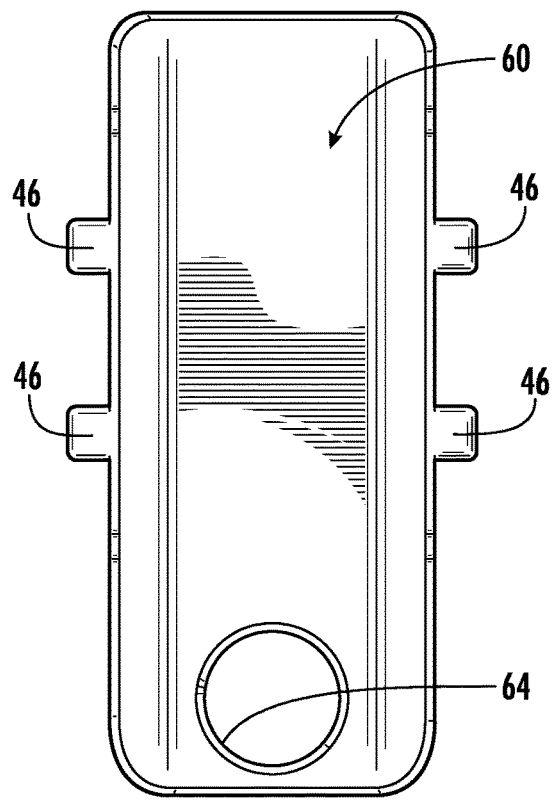
FIGS. 13A-13F are a top plan, bottom plan, right side elevation (the left side elevation being a mirror image thereof), front end elevation, rear end elevation and a longitudinal cross-section view, respectively, of a platform for use with the shoulder immobilizer as shown in FIG. 9.
Figure 13B:
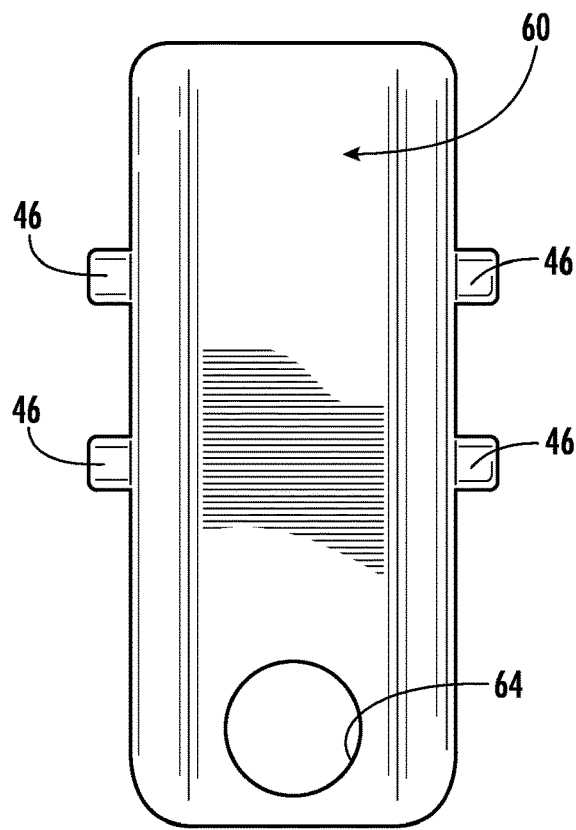
Figure 13C:
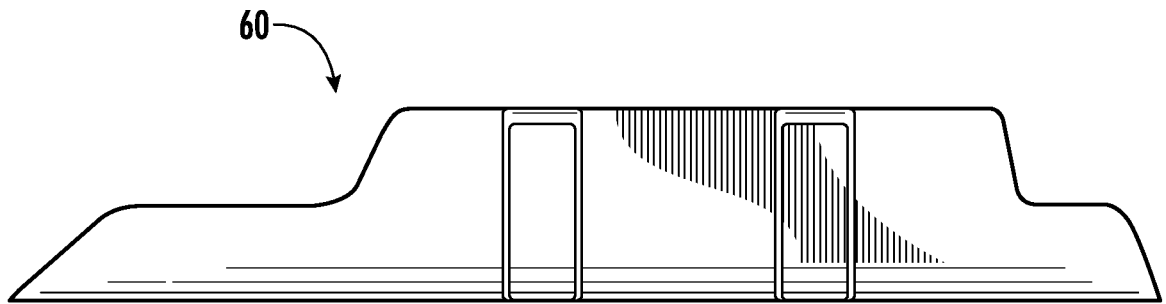
Figure 13D:
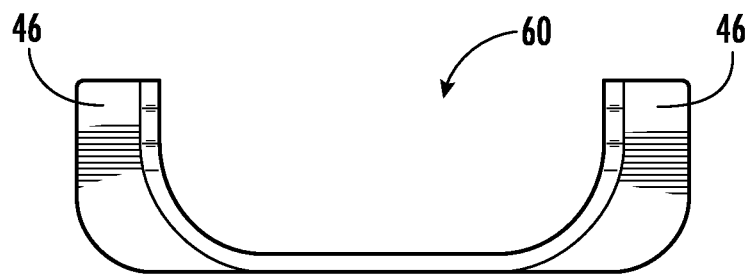
Figure 13E:
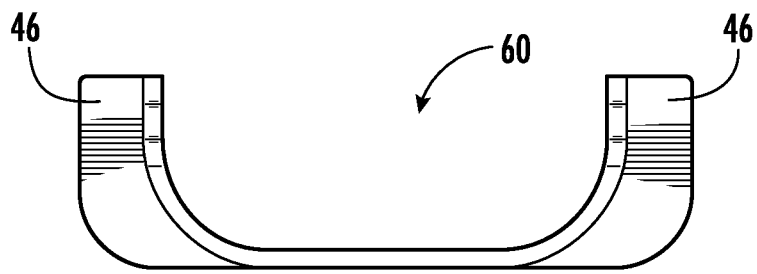
Figure 13F:
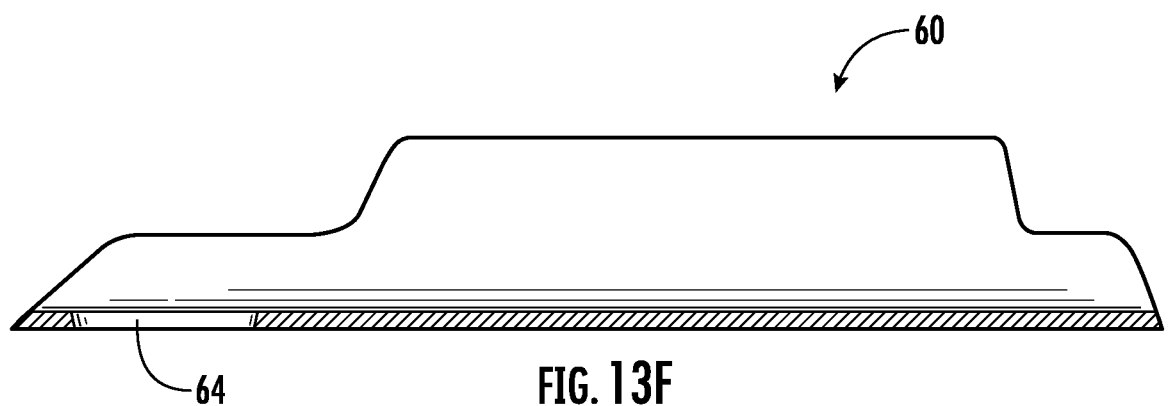
Figure 13G:
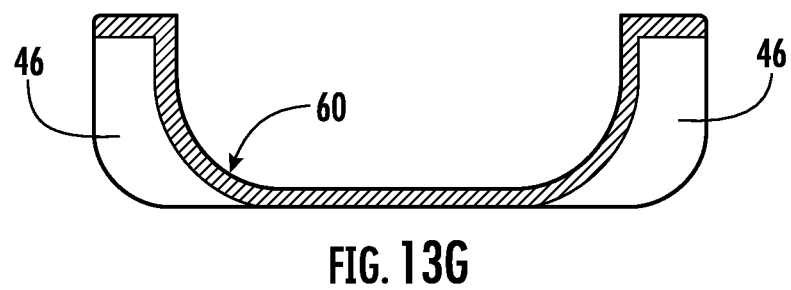
FIG. 13G is a transverse cross-section of the platform taken alon along line 13G-13G in FIG. 13B.

Referring now to the drawings, wherein like reference numbers refer to the same or similar elements throughout the several views, an embodiment of a device for immobilizing a shoulder is shown in FIG. 1 and generally designated at 20. The shoulder immobilizer 20 comprises a contoured elongated platform 22 for receiving and supporting an arm and shoulder 100 of a user in combination with an anchoring waist belt 24, and a foam wedge 26. The wedge 26 fits between the platform 22 and the torso 102 of the user. A pivoting connection assembly 30 secures the platform 22 to the belt 24 on either the right side or the left side of the user. A forearm strap 32 secures the forearm 104 to the platform 22. A second strap 34 secures the platform 22 to the belt 24 with the wedge 26 between the platform and the torso 102 of the user. The shoulder immobilizer 20 is configured to maintain the arm and shoulder 100 at desired angles of abduction and external rotation. Those of skill in the art will appreciate that the shoulder immobilizer 20 is capable of maintaining the arm at virtually any angle of abduction, extension or rotation, the magnitude of each of these angles being primarily dependent upon the size and shape of the wearer and the size and shape of the wedge 26. A preferred external rotation is about 30 degrees, which is neutral rotation with respect to the scapula. It is understood the device is also able to accommodate increased external rotation angles if necessary.

The platform 22 is a rigid, generally rectangular dish including a base portion 21 and peripheral upwardly extending side walls 23 contiguous with the base portion 21 forming a shell. The walls 23 are generally parallel with one another. The platform 22 is configured to receive and partially enclose and support the forearm of the user. The platform 22 defines opposed anterior slots 36 and posterior slots 38 in each side wall 23 of the platform. The slots 36, 38 allow straps to pass through for securing the forearm 104 to the platform 22 or for connecting the platform 22 to the belt 24, as will be described below. Spaced vents 40 extend longitudinally along the platform for air circulation to ensure that the shoulder immobilizer 20 can be worn in the hotter climates and allow air to pull away heat from the forearm 104.

A forearm strap 32 threads through the posterior slots 38 of the platform and over the forearm. The forearm strap secures the forearm in a stationary position on the platform 22 and prevents sliding. The free end of the forearm strap can be folded back onto itself and attached firmly in place on the strap by means of a complementary hook and loop fastener components on the surfaces of the strap. This arrangement allows the length forearm strap to be adjusted for a snug fit.

The waist belt 24 is the anchoring component of the shoulder immobilizer 20. The belt 24 is an elongated strap having inner and outer surfaces and first and second ends and is fitted with suitable securing means for attachment to the waist of a user. The belt 24 is configured to wrap around the torso of the user and releasably secure the platform 22 to the user through the connecting system for supporting the weight of the supported arm. Both surfaces of the belt include complementary hook and loop fastener components. The ends of the belt may thread through a D-ring (not shown) and fold back onto intermediate portions of the belt itself such that the hook and loop surfaces on the surfaces matingly engage one another. A length of the belt may thus be conveniently adjusted to tighten or loosen the belt by varying the points at which the ends engage the complementary surfaces such that the belt 24 snugly encircles the waist of the user. Although the belt 24 may be formed from any suitable material, the belt is preferably formed from an elasticized or woven knitted material. The belt 24 has a large surface area to provide mounting and load distribution. Loading over an extensive area including the torso of the wearer eliminates point loading which in turn improves patient tolerance. The belt fits the user body to provide a brace or foundation against the platform 22 is supported.

The wedge 26 comprises a block of lightweight, soft and resilient material, such as foam, to provide comfort to the user. The foam wedge 26 is positioned between the platform 22 and the torso of the user to maintain an optimum adduction and rotation close to neutral with respect to the shoulder. A lateral side surface 42 of the wedge 26 is flat for contacting the side wall 21 of the platform 22. A medial side surface 44 of the wedge 226 s contoured to fit against and conform to the torso 52 of the user along the hip. The wedge 26 is generally triangular such that the distance between the anterior edges of the medial and lateral surfaces 42, 44 is greater than a distance between the posterior edges of the medial and lateral surfaces. While the wedge 26 may be formed from any suitable materials, the wedge 26 is preferably formed from a flexible substance such as the foam material, and may be covered with an elasticized or woven knitted material. Furthermore, while the wedge 26 may have any suitable shape, the wedge preferably has a polygonal shape.

The relative positions and orientations of the lateral surface 42 and the medial surface 44 of the wedge 26 determine the angles of abduction, adduction and external rotation of the arm when the device 10 is worn. The shoulder immobilizer further functions to restrain the shoulder and arm at the desired angles. The magnitude of these angles depnds upon the size and shape of the wedge and the wearer.

The connecting system assembly 30 connects the platform 22 to the belt 24. The assembly comprises a female receiver 46 on each side the of the posterior of the platform 22 and a belt clip 50. The receiver defines a generally cylindrical slot 48. The belt clip 50 has opposed inwardly extending flanges 52 for attaching the belt clip 50 to the belt 24. The outer side of the belt clip has a cylindrical lug 54. The slot 48 is configured to receive the lug 54 for attaching the platform 22 to the belt 24. Moreover, the arrangement allows for pivotal movement of the platform 22 relative to the belt 24. In this manner, the connecting assembly is used to grip the belt and hold the platform 22 and the wedge 26 in place against the torso of the wearer to ensure that the shoulder is immobilized, supported and maintained in a desired position and optimal healing angle via rotation at the connection.

A second elongated support strap 34 of elasticized fabric material is threaded through one of the anterior slots 36 in the upper edge of the platform 22 and extends from the platform 22 and is looped around the belt 24 to pinch the wedge 26 in place while also giving the arm a level of support necessary for healing. The second strap 34 includes inner and outer surfaces and first and second ends. The strap has complementary hook and loop material on the surfaces. The strap 34 wraps around the belt 24 and is folded back on itself for releasably engaging the hook and loop material and securing the strap 34 in a loop around the belt 24. Thus, a length of the support strap 34 is conveniently adjusted so that the wedge 26 fits snugly against the wearer's torso. Loping the support strap around the belt 24 in this manner causes the wedge 26 to be drawn against the torso and provides support for the arm and shoulder of the user.

In use, to immobilize the right arm and maintain the shoulder in a desired position, the ends of the belt 24 are brought around the waist of the user and through a D-ring and secured around the user. The complementary hook and loop fasteners allow each end of the belt 24 to fold over on itself and connect to the outer surface of the belt 24 after the length has been adjusted for a snug fit. The user places the forearm 104 on the platform 22. The forearm strap 32 is passed through the posterior slots 38 and wrapped over the forearm, and the strap is fixed firmly in place by engagement of the fastener components. The belt clip 50 is attached onto the belt 24 and the lug 54 slides into the cylindrical slot 48 in the receiver 46 on the platform 22. As described above, this connection provides a pivot point for user customizability. The wedge 26 is positioned against the hip beneath the treatment shoulder between the platform 22 and the torso with the wedge medial surface abutting the hip and torso and the lateral surface along the edge of the platform. Once the wedge is properly positioned, the support strap 34 interconnecting the platform 22 and the belt 24 waist strap is looped through an anterior slot 36 and around the belt and fixed snugly in place. This completely immobilizes the arm and shoulder of the patient and draws the wedge 26 against the torso with the platform 22 pinching the wedge 26 between the belt 24 and the platform 22. The connection assembly 30 is configured to hold the platform 22 is in a substantially horizontal position relative to a standing wearer. This point provides a support against the body and to the waist of the user, as well as holding the arm in the correct position in regards to the shoulder rotation and alignment with the ground at the desired angles of abduction and external rotation.

The dimensions of the shoulder immobilizer 20 will change to accommodate different sized individuals, while the relative proportions of the components will remain the same. The immobilizer 10 may be preferably available in a variety of sizes to fit wearers of different sizes. Moreover, it is understood the shoulder immobilizer 10 can be used to treat either the right shoulder or the left shoulder. The drawings illustrate the immobilizer 10 in a right-handed configuration. A symmetrical arrangement of the parts of the shoulder immobilizer 20 allows for the same device to be used on either the right side shoulder of the left side shoulder when reversed or flipped. The immobilizer 10 is easily converted to a left-handed configuration by removing the straps 11, 32 from the platform and flipping the wedge 26 over so that it is adapted to rest against the left side of the user. The receiver on the other side of the platform 22 is used to connect to the belt 24.

A second embodiment of a platform for use with the shoulder immobilizer is shown in FIGS. 9-13 and generally designated at 60. In this embodiment, a ball 62 is received in a circular opening 64 at the anterior end of the platform 60. The ball 62 comprises a resilient and compressible material and is used to position the arm in a correct position. This is important for the correct healing location of the arm and to prevent slippage during usage. The interface between the ball 62 and the opening includes hook and loop fasteners, such as Velcro, to releasably secure the ball 62 on the platform 22. It is understood that any other hand grip may be used as long as it is suitable for securing the forearm on position and preventing anterior slippage of the arm.

Figure 14A:
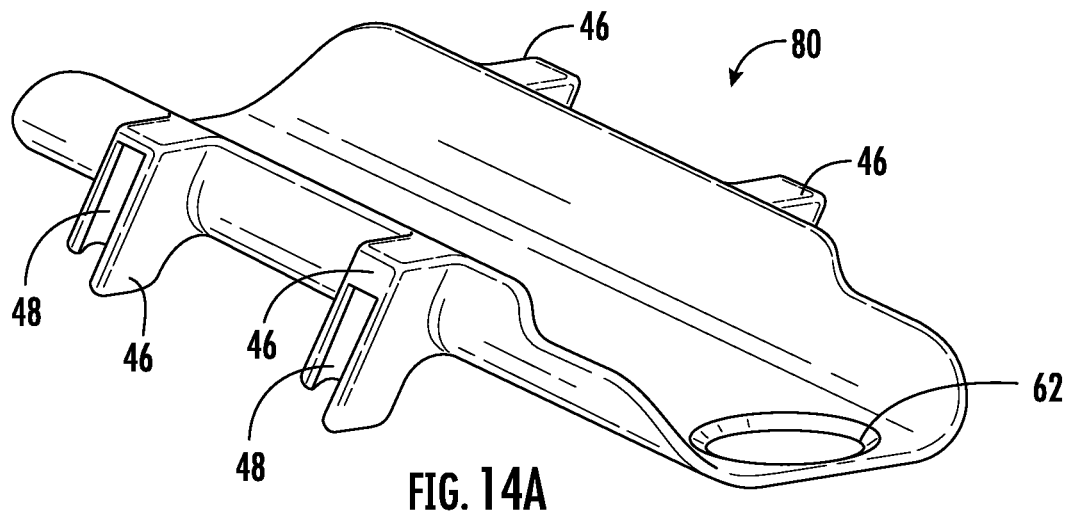
FIGS. 14A and 14B are a perspective view and a right side elevation view of another embodiment of a platform for use with the shoulder immobilizer as shown in FIG. 9.
Figure 14B:
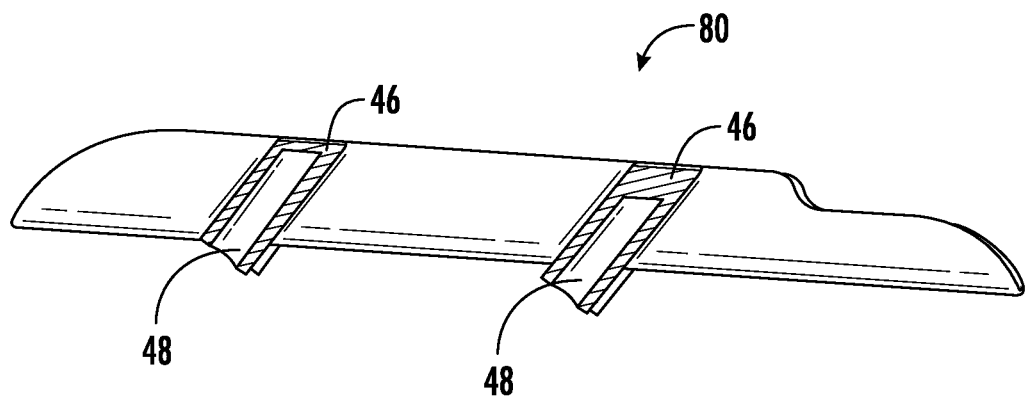
Figure 15A:
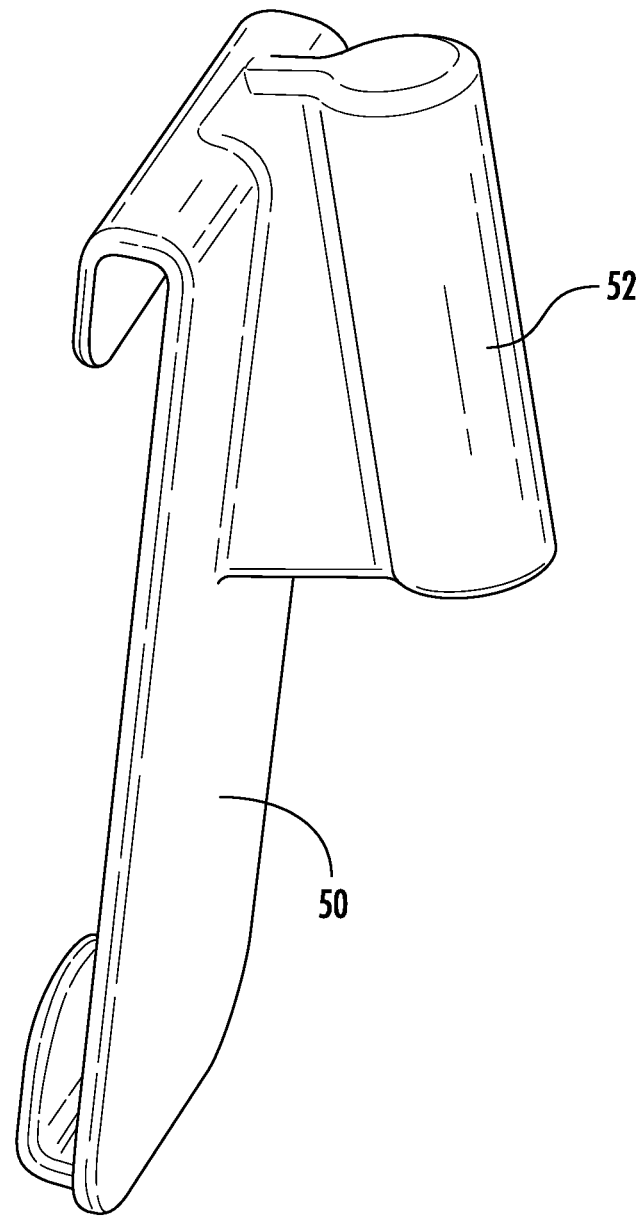
FIGS. 15A and 15B are a perspective view and a side elevation view, respectively, of another embodiment of a belt clip for use with the shoulder immobilizer as shown in FIGS. 1, 9 and 14A-14B.
Figure 15B:
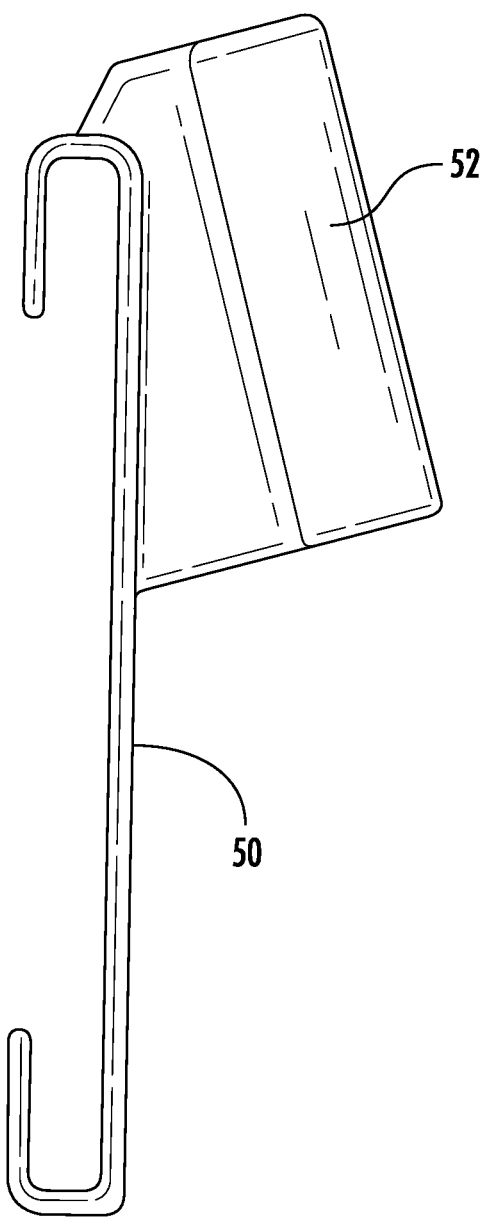

Referring to FIGS. 14A and 14B, another embodiment of a platform is shown for use with the shoulder immobilizer. In this this embodiment, the receivers 46 are angled with respect to the platform 22. In use, when connected to the belt clips 50, the anterior end of the platform 22 will be higher than the posterior end of the platform 22. The relative height of the platform 22 to the belt 24 may also be adjusted by using a belt clip 50 as shown in FIGS. 15A and 15B. This embodiment of the belt clip 50 is longer and supports a lug 52 higher on the body of the belt clip 50.

The shoulder immobilizer 10 has many advantages, including a platform 22 for supporting the arm in a stable position that allows for rapid customization of healing angle of the arm off the body. There are no shoulder straps for support since the configuration of the immobilizer 10 gains sufficient support from the waist. The shoulder immobilizer 10 support distributes the weight of the abducted upper arm around the waist rather than over the uninjured shoulder and against the wearer's neck. The wedge at the anterior portion of the torso provides the optimal angle of healing and compliance to varying body types. Thus, the shoulder immobilizer 10 offers greater comfort and simpler usage which leads to greater compliance from the patient.

We claim:

1. A shoulder immobilization device configured for immobilizing a shoulder joint and associated upper arm and forearm of a human patient in a selected relative position, the shoulder immobilization device comprising:
    a platform including
        a planar base portion and a pair of opposed parallel side walls extending upwardly from longitudinal edges of the planar base portion, the platform configured for supportively receiving and at least partially enclosing the forearm of the patient;
    a first mount defining a terminal slot integral with at least one side wall of the pair of opposed parallel side walls;
    a belt for securing around a waist of the patient; and
    a belt clip configured for attaching between the belt at a side of a body of the patient corresponding to the shoulder joint to be supported and the platform, the belt clip including a lug projecting outwardly from the belt clip and corresponding in size and shape to the terminal slot for insertion into the terminal slot, wherein the platform is suspended from the belt.

2. The shoulder immobilization device as recited in claim 1, further comprising a second mount integral with the at least one side wall and anteriorly spaced from the first mount, the second mount defining a second terminal slot.

3. The shoulder immobilization device as recited in claim 2, further comprising a second belt clip configured for attaching between the belt at the side of the body corresponding to the shoulder joint to be supported and the second mount on the platform, the second belt clip including a lug projecting outwardly from the second belt clip and corresponding in size and shape to the second terminal slot in the second mount.

4. The shoulder immobilization device as recited in claim 3, wherein the first and second mounts are non-orthogonal with the planar base portion of the platform such that an anterior of the platform is higher than a posterior of the platform when suspended from the belt.

5. The shoulder immobilization device as recited in claim 4, further comprising an opposed pair of mounts integral with the opposite side wall of the pair of opposed parallel side walls, each of the opposed pair of mounts defining a terminal slot.

6. The shoulder immobilization device as recited in claim 1, further comprising a resilient wedge configured for disposing between the platform and a torso of the patient, the resilient wedge having a medial surface for abutting the torso of the patient and a lateral surface for operatively contacting the platform.

7. The shoulder immobilization device as recited in claim 6, wherein the platform has an anterior slot, and the shoulder immobilization device further comprises a strap for passing through the anterior slot and around the belt configured for securing the resilient wedge and the platform to the patient.

8. The shoulder immobilization device as recited in claim 7, wherein the platform has a second anterior slot configured for use on the opposite side of the body.

9. The shoulder immobilization device as recited in claim 6, wherein the platform and the resilient wedge retain the wearer's arm in a position of at least about 30° of external rotation up to about 45° of external rotation.

10. The shoulder immobilization device as recited in claim 1, further comprising a hand grip adjacent an anterior end of the platform configured for preventing the forearm from moving anteriorly.

11. The shoulder immobilization device as recited in claim 10, wherein the hand grip is selected from a ball, a gel pad, a post and combinations thereof.

12. The shoulder immobilization device as recited in claim 11, wherein the anterior end of the platform defines an opening for receiving at least a portion of the ball.

13. The shoulder immobilization device as recited in claim 1, wherein the platform has opposed posterior slots in the pair of opposed parallel side walls for slidably passing a strap through the posterior slots and over the forearm configured for holding the forearm in the selected relative position.

14. The shoulder immobilization device as recited in claim 1, further comprising an opposed second mount integral with the opposite side wall of the pair of opposed parallel side walls, the second mount defining a second terminal slot.

15. The shoulder immobilization device as recited in claim 1, wherein the platform is held in a generally horizontal position.

* * * * *